(12) United States Patent
Lee et al.

(10) Patent No.: US 9,724,320 B2
(45) Date of Patent: Aug. 8, 2017

(54) COMPOSITION FOR PREVENTING OR TREATING RENAL FIBROSIS COMPRISING DIMETHYLFUMARATE AS ACTIVE INGREDIENT

(71) Applicants: KYUNGPOOK NATIONAL UNIVERSITY INDUSTRY—ACADEMIC COOPERATION FOUNDATION, Daegu (KR); KYUNGPOOK NATIONAL UNIVERSITY HOSPITAL, Daegu (KR)

(72) Inventors: In Kyu Lee, Daegu (KR); Keun Gyu Park, Daegu (KR); Chang Joo Oh, Daegu (KR); Han Jong Kim, Daegu (KR); Joon-Young Kim, Daegu (KR)

(73) Assignee: KYUNGPOOK NATIONAL UNIVERSITY INDUSTRY—ACADEMIC COOPERATION FOUNDATION, Daegu (KR)

( * ) Notice: Subject to any disclaimer, the term of this patent is extended or adjusted under 35 U.S.C. 154(b) by 0 days.

(21) Appl. No.: 14/767,767

(22) PCT Filed: Feb. 20, 2013

(86) PCT No.: PCT/KR2013/001303
§ 371 (c)(1),
(2) Date: Nov. 10, 2015

(87) PCT Pub. No.: WO2014/126285
PCT Pub. Date: Aug. 21, 2014

(65) Prior Publication Data
US 2016/0067206 A1 Mar. 10, 2016

(30) Foreign Application Priority Data
Feb. 13, 2013 (KR) .................. 10-2013-0015431

(51) Int. Cl.
*A61K 31/225* (2006.01)
*A61K 9/00* (2006.01)
*A61K 9/14* (2006.01)
*A61K 9/20* (2006.01)
*A23L 33/10* (2016.01)

(52) U.S. Cl.
CPC ............ *A61K 31/225* (2013.01); *A23L 33/10* (2016.08); *A61K 9/0053* (2013.01); *A61K 9/0095* (2013.01); *A61K 9/146* (2013.01); *A61K 9/2059* (2013.01); *A23V 2002/00* (2013.01)

(58) Field of Classification Search
CPC .................................................... A61K 31/225
See application file for complete search history.

(56) References Cited

U.S. PATENT DOCUMENTS

| | | | |
|---|---|---|---|
| 6,503,976 B2 | 1/2003 | Zuckerman et al. | |
| 2004/0054001 A1* | 3/2004 | Joshi | A61K 9/1652 514/527 |
| 2010/0324327 A1* | 12/2010 | Lee | A61K 31/225 560/190 |
| 2012/0034274 A1 | 2/2012 | Nilsson et al. | |
| 2012/0232142 A1 | 9/2012 | Lee | |

FOREIGN PATENT DOCUMENTS

| | | |
|---|---|---|
| KR | 20090028047 | 3/2009 |
| KR | 20120032372 A | 4/2012 |

OTHER PUBLICATIONS

Oh et al. PLoS One, Oct. 2012, vol. 7, No. 10, e45870, pp. 1-12 (Published Online Oct. 8, 2012).*
Valero et al. Journal of Investigative Dermatology, 2010, vol. 130, pp. 1087-1094.*
Mrowietz et al. Trends in Molecular Medicine, Jan. 2005, vol. 11, No. 1, pp. 43-48.*
International Preliminary Report on Patentability (English translation), International Application No. PCT/KR2013/001303, mailed Aug. 18, 2015.
International Search Report and Written Opinion (English translation), International Application No. PCT/KR2013/001303, mailed Oct. 30, 2013.

* cited by examiner

*Primary Examiner* — James D Anderson
(74) *Attorney, Agent, or Firm* — Marshall, Gerstein & Borun LLP

(57) ABSTRACT

The present invention relates to a composition for preventing or treating renal fibrosis comprising dimethylfumarate (DMF) as an active ingredient. The DMF according to the present invention has an excellent effect of reducing renal fibrosis by activating Nrf2 to inhibit TGF-β/Smad signaling, and thus is useful for preventing or treating renal fibrosis.

2 Claims, 6 Drawing Sheets

COMPOSITION FOR PREVENTING OR TREATING RENAL FIBROSIS COMPRISING DIMETHYLFUMARATE AS ACTIVE INGREDIENT

TECHNICAL FIELD

The present invention relates to a composition for preventing or treating renal fibrosis, which includes dimethylfumarate (DMF) as an active ingredient.

BACKGROUND ART

Fibrosis is a disease characterized by excessive deposition of connective tissue proteins contributing to abnormal extracellular matrix (ECM) metabolism in organs such as skin, lungs, heart, liver, kidney, etc. Fibrosis can reduce the number of healthy cells in any organs or tissues. Also, an increase in mass of fibrotic connective tissues may cause damage to normal structures of the organs or tissues. Such damage may weaken the physiological and biochemical functions of the affected organs or tissues, and completely ruin the organs. Research on pathology, diagnostic methods, preventive and therapeutic methods for treating fibrosis in organs and tissues has been widely conducted. However, there are still many challenges, especially in the field of development of effective therapeutic agents.

A mechanism of fibrosis formation has not been sufficiently elucidated so far. However, the fibrosis in the organs and tissues is generally caused by combined factors, for examples, inflammations, immunological responses, ischemia, hemodynamic changes, etc. (which result in inflammatory degeneration and necrosis in soft tissue cells). As a result, the affected soft tissue cells activate macrophages to release a large number of cytokines and growth factors. Among these, transforming growth factor-beta (TGF-β) plays an important role. TGF-β can activate the resting ECM components to generate cells, which can be converted into myofibroblasts. The newly formed fibroblasts increase the production of collagen that is a core protein of ECM, and also decrease the destruction of ECM. As a result, the ECM components are accumulated, thereby inducing the formation of fibrosis in organs or tissues. Thus, the onset and progression of fibrosis in organs or tissues result from inflammatory responses and the production of inflammatory cytokines, mainly TGF-β. Owing to the critical role of TGF-β in the ECM accumulation and the formation of fibrosis in the organs or tissues, it was logically an important goal to screen for compounds capable of inhibiting the production of pro-inflammatory cytokines, TGF-β, in an early stage of development of anti-fibrotic drugs.

Meanwhile, dimethylfumarate (DMF) is known as a substance that activates a transcriptional regulatory factor, Nrf2, which plays an important role in the production of antioxidant enzymes and phase II detoxification enzymes in cells in response to external oxidative stress. Also, DMF is a drug that is used to treat skin diseases such as psoriasis, has a therapeutic effect in treating multiple sclerosis, and is in a clinical trial stage. Also, DMF is reported to inhibit the metastasis of cancer and suppress the proliferation of cancer cells, but no research on DMF having an effect in treating and improving renal fibrosis has yet been reported.

Accordingly, the present inventors have made a great effort to develop novel therapeutic agents for treating renal fibrosis, and found that DMF has an effect in alleviating renal fibrosis by activating Nrf2. Therefore, the present invention has been completed based on these facts.

DISCLOSURE

Technical Problem

An embodiment of the present invention is directed to a pharmaceutical composition for preventing or treating renal fibrosis, which includes dimethylfumarate (DMF) as an active ingredient.

Another embodiment of the present invention is directed to a food composition for preventing or treating renal fibrosis, which includes DMF as an active ingredient.

Technical Solution

According to an aspect of the present invention, there is provided a pharmaceutical composition for preventing or treating renal fibrosis, which includes dimethylfumarate (DMF) as an active ingredient.

According to another aspect of the present invention, there is provided a food composition for preventing or treating renal fibrosis, which includes DMF as an active ingredient.

Advantageous Effects

According to exemplary embodiments of the present invention, the DMF has an excellent therapeutic effect of reducing renal fibrosis by activating Nrf2 to inhibit TGF-β/Smad signaling, and thus is useful for preventing or treating renal fibrosis.

BEST MODE FOR THE INVENTION

Figure 1:
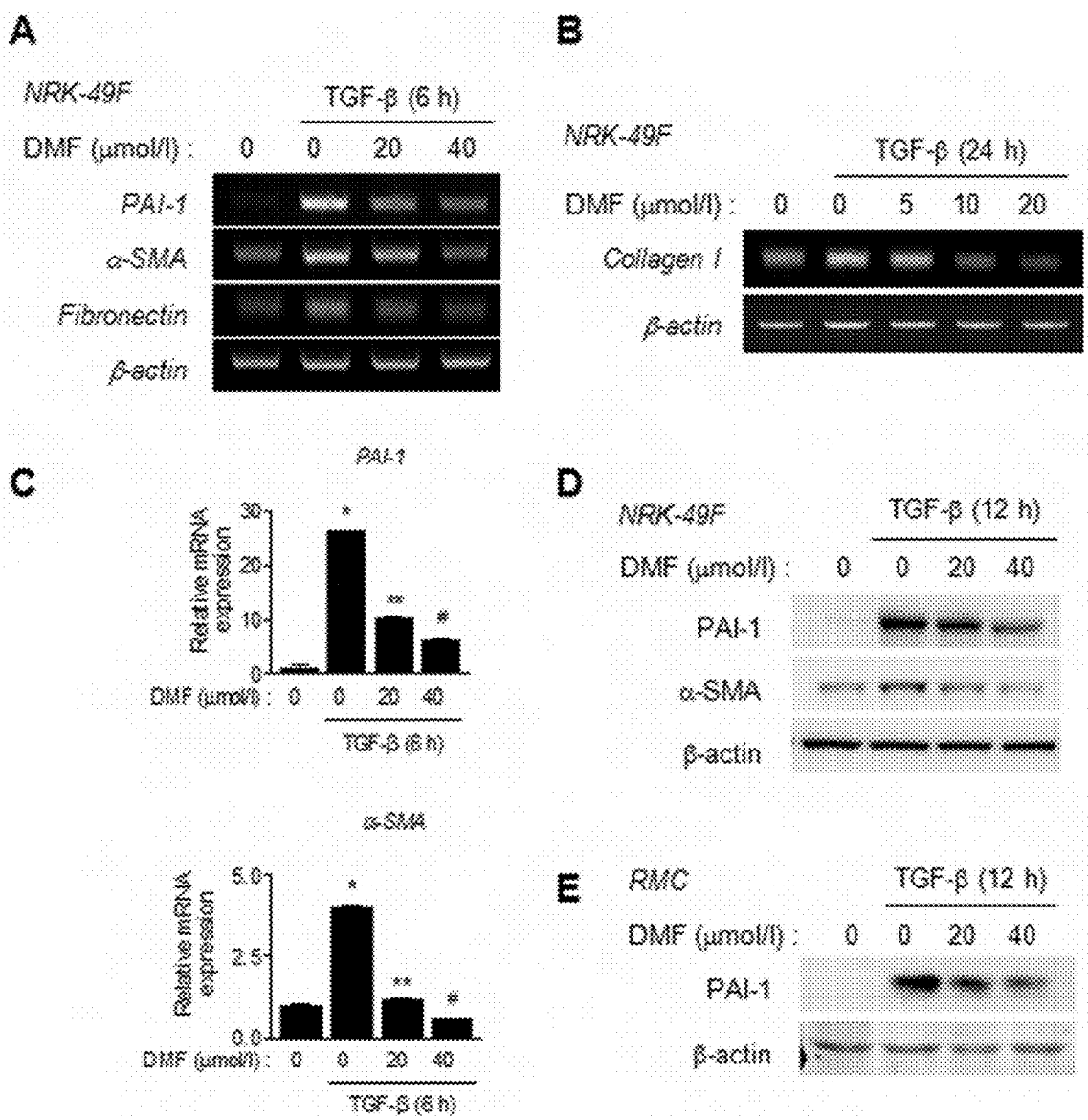
FIG. 1 is a diagram showing effects of dimethylfumarate (DMF) on expression of plasminogen activator inhibitor 1 (PAI-1), alpha-smooth muscle actin (α-SMA), fibronectin, and collagen type I

Exemplary embodiments of the present invention will be described below in more detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Throughout the disclosure, like reference numerals refer to like parts throughout the various figures and embodiments of the present invention.

The present invention provides a composition for preventing or treating renal fibrosis, which included dimethylfumarate (DMF) as an active ingredient.

The composition includes a pharmaceutical composition, or a food composition.

Hereinafter, the present invention will be described in further detail.

The DMF according to one exemplary embodiment of the present invention reduce TGF-β/Smad3 signaling by increasing expression of Nrf2, and alleviates renal fibrosis by inhibiting expression of an extracellular matrix. Therefore, the DMF according to one exemplary embodiment of the present invention may be used as a medicine or a health food useful for preventing or treating renal fibrosis.

The composition according to one exemplary embodiment of the present invention may include at least one known active ingredient having an effect of preventing or treating renal fibrosis in addition to the DMF.

The composition according to one exemplary embodiment of the present invention may be prepared to further include at least one pharmaceutically acceptable carrier in addition to the above-described active ingredient for administration. The pharmaceutically acceptable carrier that may be used herein may include saline, sterile water, a Ringer's solution, buffered saline, a dextrose solution, a maltodextrin solution, glycerol, ethanol, and a combination thereof, and may further include other conventional additives such as an antioxidant, a buffer, a bacteristat, and the like, when necessary. Also, a diluent, a dispersant, a surfactant, a binder, and a lubricant may be further added to the composition, which may then be formulated into injectable formulations such as an aqueous solution, suspension, and an emulsion, pills, capsules, granules, or tablets. Further, the compositions may be preferably formulated using proper methods known in the art, or a method disclosed in Remington's Pharmaceutical Science (recent edition), Mack Publishing Company, Easton Pa., depending on the respective diseases or components.

The composition of the present invention may be administered orally or parenterally (for example, intravenously, subcutaneously, intraperitoneally, or by topical application) according to a desired method, and a dosage of the composition may be adjusted to a wide extent according to the body weight, age, gender, and health condition of a patient, a diet, an administration time, a method of administration, an excretion rate, the severity of a disease, etc. The daily dose of the DMF may be in a range of approximately 10 to 100 mg/kg, preferably approximately 25 to 50 mg/kg. In this case, the DMF is preferably administered once a day, or administered in divided doses.

The composition of the present invention may be used alone to prevent or treat renal fibrosis, or may be used in combination with surgery, hormone treatment, medication, and methods using a biological response modifier.

The DMF of the present invention may be added to a health functional food for the purpose of preventing or improving renal fibrosis. When the DMF of the present invention is used as a food additive, the DMF may be added per se, or may be used in combination with other foods or food components. In this case, the DMF may be used at a proper amount according to a conventional method. An amount of the mixed active ingredient may be properly determined according to a purpose of use (prophylaxis, health, or therapeutic treatment). Upon preparation of foods or drinks, the composition according to one exemplary embodiment of the present invention is generally added at a content of 15% by weight or less, preferably 10% by weight or less, based on the total amount of the ingredients. However, when the composition is ingested for a long period of time for the purpose of health and hygiene or health control, the dose of the composition may fall within this range. Also, the active ingredient may be used at a dose exceeding this range since the active ingredient has no problem in an aspect of safety.

The types of foods are not particularly limited. Examples of the foods to which the active ingredient may be added may include meats, sausages, breads, chocolates, candies, snacks, confectionery, pizzas, ramen, other noodles, gums, dairy products including ice creams, various soups, beverages, teas, drinks, alcoholic beverages, and vitamin combinations. In the typical meanings, the foods include all kinds of health functional foods.

Health drink composition according to one exemplary embodiment of the present invention may include a variety of flavoring agents or natural carbohydrates as additional components as in the conventional beverages. The above-listed natural carbohydrates that may be used herein may include monosaccharides such as glucose, and fructose, disaccharides such as maltose, and sucrose, polysaccharides such as dextrine, and cyclodextrine, and sugar alcohols such as xylitol, sorbitol, erythritol, and the like. Natural sweetening agents such as thaumatin, and stevia extracts, or synthetic sweetening agents such as saccharine and aspartame may be used as the sweetening agents. The natural carbohydrates are generally added at a content of approximately 0.01 to 0.20 g, preferably approximately 0.04 to 0.10 g, based on 100 mL of the composition according to one exemplary embodiment of the present invention.

In addition to the above-described components, the composition according to one exemplary embodiment of the present invention may include various nutritional supplements, vitamins, electrolytes, flavoring agents, coloring agents, pectic acid and salts thereof, alginic acid and salts thereof, organic acids, protective colloidal thickeners, pH regulators, stabilizing agents, preservatives, glycerin, alcohol, carbonating agents used for carbonated drinks, and the like. In addition, the composition according to one exemplary embodiment of the present invention may include fruit pulps for preparing natural fruit juices, fruit juice drinks, and vegetable-based beverages. Such a component may be used alone or in combination. The content of such additives is of no great importance, but may be generally selected in a range of 0.01 to 0.20 parts by weight, based on 100 parts by weight of the composition according to one exemplary embodiment of the present invention.

MODE FOR THE INVENTION

Hereinafter, preferred embodiments will be provided to aid in understanding the present invention. However, it should be understood that detailed description provided herein is merely intended to provide a better understanding of the present invention, and is not intended to limit the scope of the present invention.

Example 1: Determination of Effect of DMF on Inhibition of Expression PAI-1, α-SMA, Fibronectin, and Collagen Type I by TGF-β

1. Determination of Expression Levels of PAI-1, α-SMA, Fibronectin, and Collagen Type I Upon Treatment with DMF To determine expression levels of plasminogen activator inhibitor 1 (PAI-1), alpha-smooth muscle actin (α-SMA), fibronectin, and collagen I upon treatment with DMF, the following experiment was performed. First, renal fibroblast cells (NRK-49F) were starved for 12 hours, and treated with DMF for 1 hour. Thereafter, the renal fibroblast cells were treated with TGF-β (2 ng/ml), and subjected to semi-quantitative RT-PCR to determine whether the expression of extracellular matrices such as PAI-1, α-SMA, fibronectin, and collagen type I was decreased by DMF. These experimental results are shown in FIG. 1A (6 hours), and FIG. 1B (24 hours).

As shown in FIGS. 1A and 1B, it was revealed that the expression levels of PAI-1, α-SMA, fibronectin, and collagen type I were reduced in the DMF-treated group, compared to the control in which the renal fibroblast cells were not treated with DMF.

2. Determination of Relative mRNA Expression Levels of PAI-1 and α-SMA Upon Treatment with DMF NRK-49F cells were treated with DMF for 1 hour, and then stimulated with TGF-β, (2 ng/ml) for 6 hours. Thereafter, the mRNA expression levels of PAI-1 and α-SMA were analyzed using real-time RT-PCR to determine effects of DMF. The data were obtained from independent experiments conducted in triplicate, and the average±SEM (standard deviation) was as follows: *P<0.01 vs. control; **P<0.01, #P<0.001 vs. TGF-β-stimulated (Top panel of FIG. 1C); *P<0.001 vs. control; **P<0.01, #P<0.001 vs. TGF-β-stimulated (Bottom panel of FIG. 1C). These experimental results are shown in FIG. 1C.

As shown in FIG. 1C, it was revealed that the expression levels of PAI-1 and α-SMA were significantly reduced in the case of the DMF-treated group, compared to the control in which the renal fibroblast cells were not treated with DMF.

3. Determination of Effect of DMF on Expression of PAI-1.

NRK-49F cells stimulated with TGF-β, and rat mesangial cells (RMCs) were treated with DMF, and subjected to Western blot analysis to determine the expression of PAI-1. These experimental results are shown in FIGS. 1D (NRK-49F) and 1E (RMC).

As shown in FIGS. 1D and 1E, it was revealed that the expression of PAI-1 was significantly reduced in the DMF-treated group, compared to the control in which both of the NRK-49F and RMC cells were not treated with DMF.

Example 2: Determination of Effect of DMF on Reduction in TGF-μ/Smad3 Signaling

1. Determination of Effect of DMF on PAI-1-Luc and (CAGA)$_9$ MLP-Luc Reporter Constructs Stimulated by TGF-β

AD-293 cells were transfected with a PAI-1-Luc or (CAGA)$_9$ MLP-Luc plasmid containing ALK5 (TGF-β construct active type I receptor) or no ALK5 for 24 hours. The transfected cells were deficient in nutrition for 12 hours, and stimulated with TGF-β (2 ng/ml) for 5 hours. Then, RLU values were measured. The data were obtained from independent experiments conducted in triplicate, and the average±SEM (standard deviation) was as follows: (A) *P<0.001 vs. reporter alone; P<0.001, *P<0.01 vs. TGF-β-stimulated (Left portion of FIG. 2A). #P<0.05 vs. reporter alone; P<0.01, *P<0.05 vs. ALK5-stimulated (Right portion of FIG. 2A). (B) *P<0.01 vs. reporter alone; **P<0.01 vs. TGF-β-stimulated (Left portion of FIG. 2B). *P<0.01 vs. reporter alone; P<0.05, *P<0.01 vs. ALK5-stimulated (Right portion of FIG. 2B). These experimental results are shown in FIGS. 2A and 2B.

Figure 2:
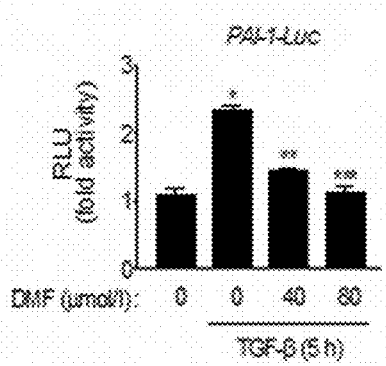
FIG. 2 is a diagram showing effects of DMF on reduction in TGF-β/Smad3 signaling.
Figure 2:
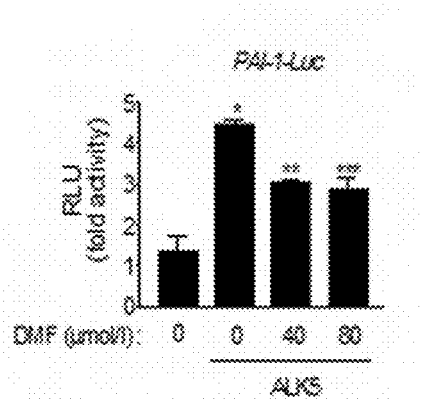
Figure 2:
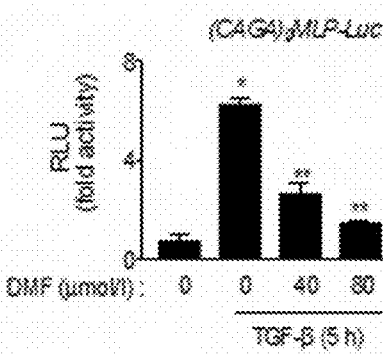
Figure 2:
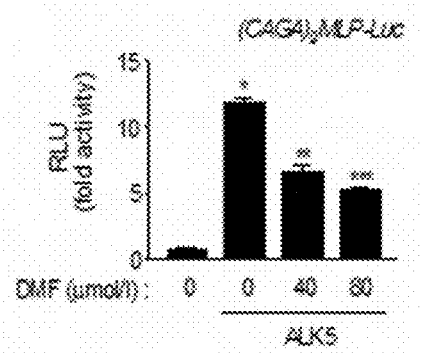
Figure 2:
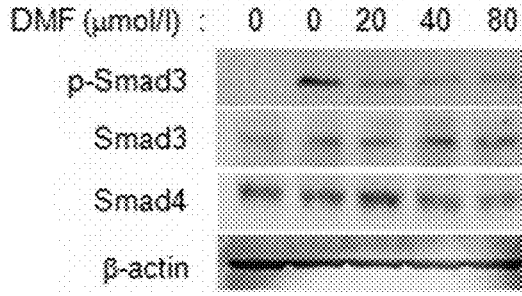
Figure 2:
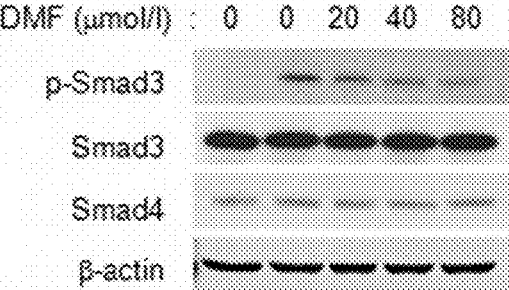
Figure 2:
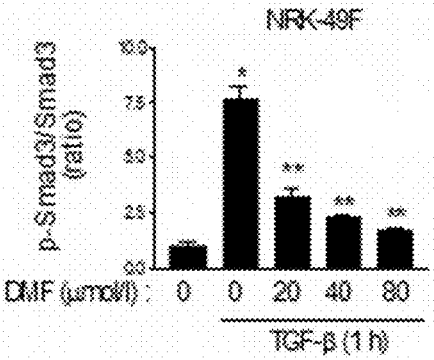
Figure 2:
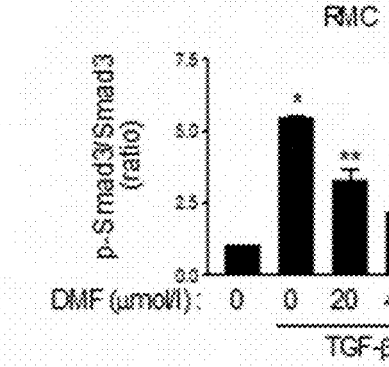

As shown in FIGS. 2A and 2B, it was revealed that, when the AD-293 cells were transfected with the PAI-1-Luc and (CAGA)$_9$ MLP-Luc plasmids, the RLU values were lower in the DMF-treated group, compared to the control which not treated with DMF.

2. Determination of Effect of DMF on Smad3 Phosphorylation Stimulated by TGF-β

An effect of DMF on Smad3 phosphorylation stimulated by TGF-β was determined using a Western blotting method. The deficient NRK-49F cells and RMCs were pre-treated with DMF for 1 hour, and then stimulated with TGF-β (2 ng/ml) for 1 hour. The data were obtained from independent experiments conducted in triplicate, and a bar graph represents the average±SEM: (C) *P<0.01 vs. control, **P<0.05 vs. TGF-β-stimulated. (D) *P<0.001 vs. control, **P<0.05, #P<0.01, #P<0.001 vs. TGF-β-stimulated. These experimental results are shown in FIGS. 2C (NRK-49F) and 2D (RMC).

As shown in FIGS. 2C and 2D, it was revealed that the phosphorylation of Smad3 stimulated by TGF-β was reduced in a DMF concentration-dependent manner.

Example 3: Effect of Nrf2 on Inhibition of Expression of PAI-1, α-SMA, Fibronectin, and Collagen Type I 1. Determination of Increase in Expression of Nrf2 Upon Treatment with DMF To elucidate the relationship between DMF (40 μmol/L) and expression of a transcription factor, Nrf2, for expression of antioxidant enzymes in RMCs and NRK-49F cells (serum-starved cells) starved in a serum-free medium, expression levels of Nrf2 in both of the cells were checked at specific time points using a Southern blotting method. These experimental results are shown in FIGS. 3A (NRK-49F cells), and 3E (RMCs).

Figure 3:
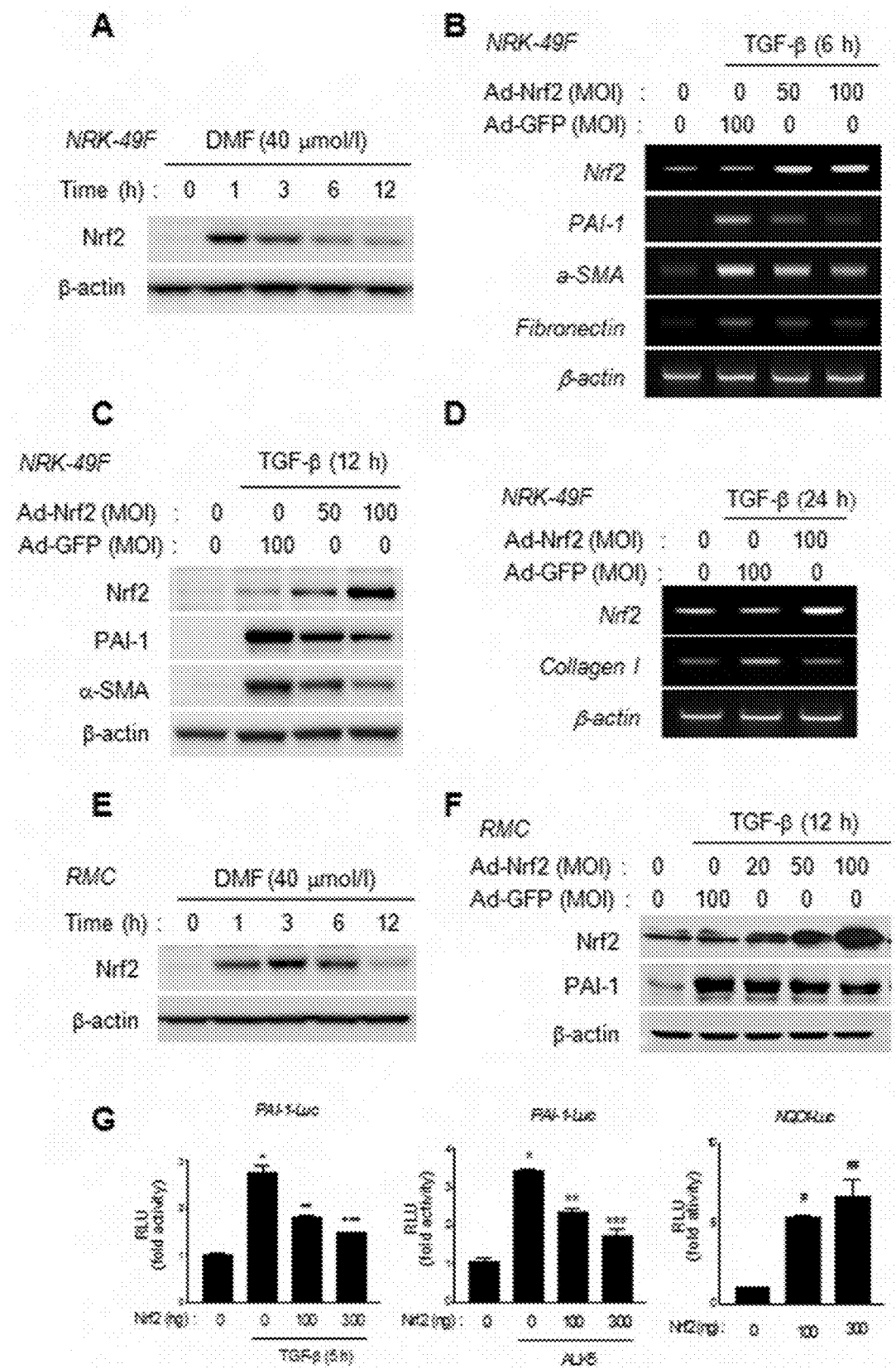
FIG. 3 is a diagram showing effects of Nrf2 on inhibition of expression of PAI-1, α-SMA, fibronectin, and collagen type I.

As shown in FIGS. 3A and 3E, it was revealed that the expression level of Nrf2 was enhanced when the cells were treated with DMF.

2. Determination of Reduction in Expression of ECM Components Upon Overexpression of Nrf2

To determine an effect on expression of ECM components (including collagen type I) in a RNA level when Nrf2 was overexpressed using adenoviruses (Ad-Nrf2), the deficient NRK-49F cells were transfected with Ad-Nrf2 for 24 hours. Thereafter, the NRK-49F cells were stimulated with TGF-β, (2 ng/ml) for 6 hours, 12 hours, or 24 hours. These experimental results are shown in FIGS. 3B (6 hours), 3C (12 hours), and 3D (24 hours).

As shown in FIGS. 3B, 3C and 3D, it was revealed that Nrf2 whose expression was enhanced by Ad-Nrf2 significantly reduced expression of the ECM components including collagen type I in a RNA level.

3. Determination of Reduction in Expression of ECM Components in RNA and Protein Levels Upon Overexpression of Nrf2

To determine an effect of adenoviruses (Ad-Nrf2) on the expression of the ECM components in protein level, RMCs stimulated with TGF-β were transfected with Ad-Nrf2, and a protein expression level of PAI-1 was determined using a Southern blotting method. Also, an effect of Nrf2 was determined using the AD-293 cells stimulated with TGF-β or ALK5. Here, the AD-293 cells were co-transfected with a PAI-1-Luc plasmid, a Nrf2-expression plasmid, and an ALK5 expression plasmid for 24 hours, or cultured for 24 hours with no plasmids, and starved for 12 hours in a serum-free medium, and then stimulated with TGF-β for 5 hours. These experimental results are shown in FIGS. 3F and 3G.

As shown in FIG. 3F, it was revealed that Ad-Nrf2 significantly reduced the expression of PAI-1.

As shown in FIG. 3G, it was also revealed that Nrf2 was stimulated with TGF-β or ALK5 to inhibit the expression of PAI-1-Luc whose expression was promoted.

Example 4: Effect of Nrf2 on Reduction in TGF-β/Smad3 Signaling

1. Determination of Effect of Ad-Nrf2 on Smad3 Phosphorylation

NRK-49F cells and RMCs were starved for 24 hours in a serum-free medium, transfected with Ad-GFP or Ad-Nrf2, and then stimulated with TGF-β for 1 hour. Thereafter, the phosphorylation levels of Smad3 expressed in both of the cells were determined using a Western blotting method. The data were obtained from independent experiments conducted in triplicate, and a bar graph represents the average±SEM: (A) *P<0.01 vs. control, P<0.05 vs. TGF-β-stimulated. (B) P<0.001 vs. control, P<0.05, #P<0.01 vs. TGF-β-stimulated. These experimental results are shown in FIGS. 4A (NRK-49F) and 4B (RMCs).

Figure 4:
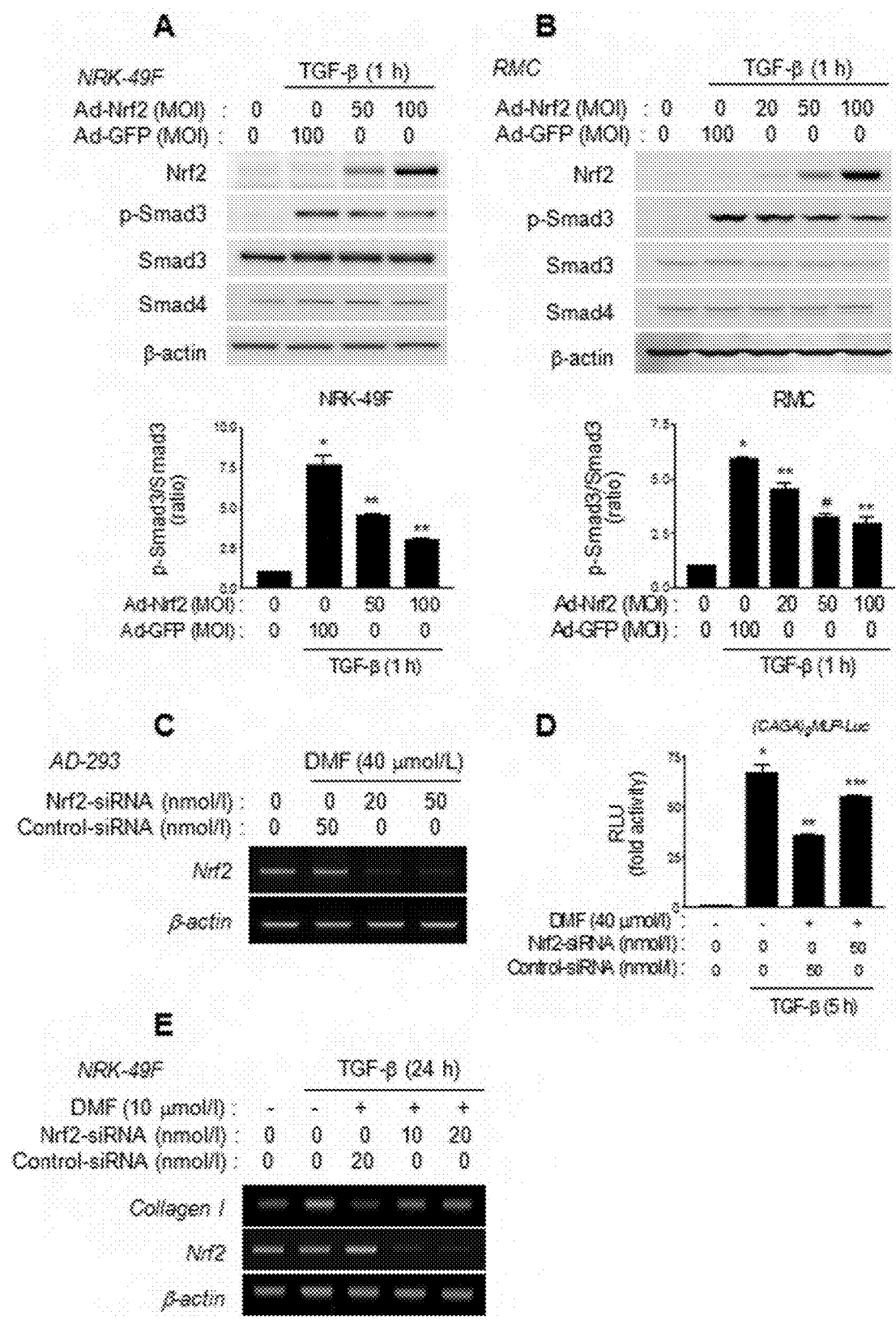
FIG. 4 is a diagram showing effects of Nrf2 on reduction in TGF-β/Smad3 signaling.

As shown in FIGS. 4A and 4B, it was revealed that the expression level of Nrf2 increased and the expression level of phosphorylated Smad3 (p-Smad3) decreased with the amount of Ad-Nrf2 increased (Top panel). Also, it was revealed that the ratio of p-Smad3 and Smad3 was lowered when the cells were treated with Ad-Nrf2.

2. Determination of Increase in Expression of Nrf2 by Nrf2-siRNA

To determine an effect of Nrf2 whose expression was enhanced by DMF on expression of ECM components, first, it was determined whether or not the expression of Nrf2 was reduced by use of Nrf2 small interfering RNA (siRNA). This experiment was performed, as follows. AD-293 cells were transfected with Nrf2-siRNA and the control (scrambled siRNA), respectively, and then cultured for 24 hours. Thereafter, the transfected cells were cultured for 12 hours in a serum-free medium, treated with DMF (40 µmol/l) for 1 hour, and analyzed using semi-quantitative RT-PCR. These experimental results are shown in FIG. 4C.

As shown in FIG. 4C, it was revealed that, when the AD-293 cells were treated with Nrf2-siRNA, the expression of Nrf2 was significantly reduced, compared to the control.

3. Determination of Effect of Nrf2-siRNA on (CAGA)$_9$ MLP-Luc Expression

An effect of Nrf2-siRNA on (CAGA)$_9$ MLP-Luc activity (treated with TGF-β) inhibited by DMF was determined. AD-293 cells were starved for 12 hours in a serum-free medium, and then co-transfected with (CAGA)$_9$ MLP-Luc and control-siRNA or Nrf2-siRNA for 24 hours. Thereafter, the transfected cells were stimulated with TGF-β for 5 hours, and then treated with DMF (40 µmol/l) for 1 hour. The data were obtained from independent experiments conducted in triplicate, and a bar graph represents the average±SEM: *P<0.01 vs. reporter alone, P<0.05 vs. TGF-β-stimulated, *P<0.05 vs. DMF-treated control-siRNA. These experimental results are shown in FIG. 4D.

As shown in FIG. 4D, it was revealed that, when the AD-293 cells were treated with Nrf2-siRNA, the RLU value of (CAGA)$_9$ MLP-Luc was higher, compared to the control.

4. Determination of Effect of Nrf2-siRNA on Expression of Collagen Type I mRNA

An effect of Nrf2-siRNA on expression of collagen type I mRNA (treated with TGF-β) inhibited by DMF was determined. NRK-49F cells were transfected with control-siRNA and Nrf2-siRNA for 24 hours, and then starved for 12 hours. The transfected cells were pre-treated with DMF (10 µmol/L) for hour, stimulated with TGF-β, for 24 hours, and then analyzed using semi-quantitative RT-PCR. These experimental results are shown in FIG. 4E.

As shown in FIG. 4E, it was revealed that the expression level of collagen type I was recovered by addition of Nrf2-siRNA.

Example 5: Relationship Between Antioxidant Enzymes, NQO1 and HO-1, and TGF-β/Smad Signaling 1. Determination of Relationship Between DMF and HO-1 or NQO1

Expression levels of the activating enzymes, HO-1 and NQO1 in NRK-49F cells according to the DMF were determined. The cells were treated with DMF (40 µmol/L), and analyzed using semi-quantitative RT-PCR. These experimental results are shown in FIG. 5A.

As shown in FIG. 5A, it could be seen that, when the NRK-49F cells were treated with DMF, the expression levels of NQO1 and HO-1 were enhanced.

2. Determination of Effect of NQO1 and HO-1 on Downregulation of (CAGA)$_9$ MLP-Luciferase Activity An effect of siRNA on expression of NQO1 and HO-1 mRNAs in AD-293 cells were determined using semi-quantitative RT-PCR.

Figure 5:
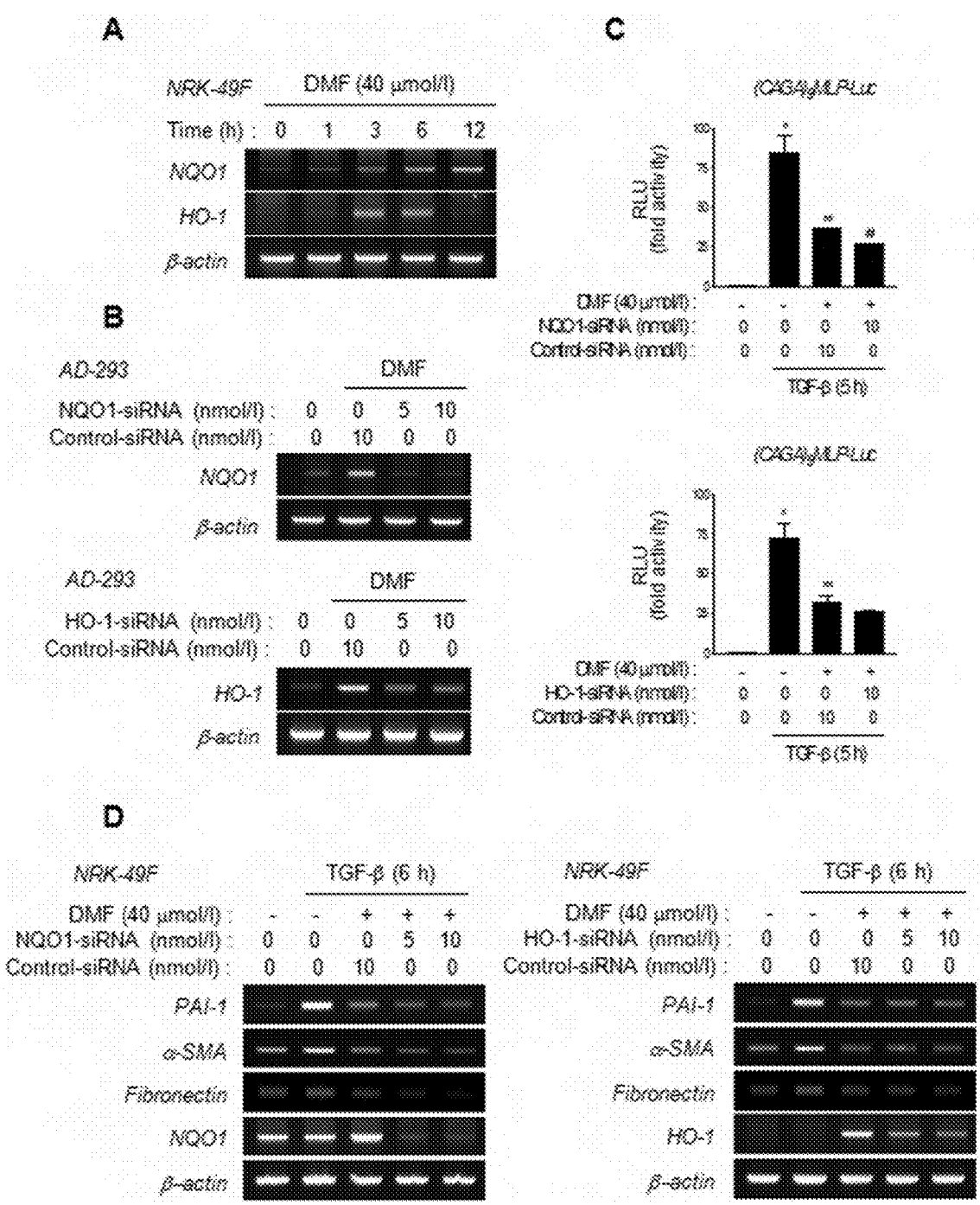
FIG. 5 is a diagram showing the relationship between antioxidant enzymes, NQO1 and heme-oxygenase-1 (HO-1), and TGF-β/Smad signaling.

Also, the AD-293 cells were temporally transfected with a (CAGA)$_9$ MLP-luc reporter construct, and NQO1 or HO-1 siRNA, and then starved for 12 hours in a serum-free medium. The transfected cells were pre-treated with DMF (40 µmol/l) for 1 hour, and then stimulated with TGF-β (2 ng/ml) for 5 hours. Thereafter, RLU values were measured. The data and average±SEM were obtained from independent experiments conducted in triplicate: (C) *P<0.05 vs. reporter alone, **P<0.05 vs. TGF-β-stimulated, #P<0.05 vs. DMF-treated TGF-β-stimulated (Top portion of FIG. 5C); *P<0.05 vs. reporter alone, **P<0.05 TGF-β-stimulated (Bottom portion of FIG. 5C). These experimental results are shown in FIGS. 5B and 5 C.

As shown in FIG. 5B, it could be seen that the expression of NQO1 and HO-1 was reduced by NQO1 and HO-1 siRNAs.

As shown in FIG. 5C, it could be also seen that the (CAGA)$_9$ MLP-luc promoter activity reduced by DMF was not recovered by these siRNAs.

3. Determination of Effect of NQO1 and HO-1 siRNAs on Extracellular Matrix

It was determined whether DMF-mediated inhibition of mRNA expression of PAI-1, α-SMA, and fibronectin in NRK-49F cells stimulated with TGF-β was knocked down by NQO1 or HO-1. NRK-49 cells were transfected with NQO1 or HO-1 siRNA for 24 hours. NRK-49F cells were starved in a serum-free medium, and then the starved cells were pre-treated with DMF (40 µmol/L) for 1 hour, stimulated with TGF-β, (2 ng/ml) for 6 hours, and analyzed using semi-quantitative RT-PCR. These experimental results are shown in FIG. 5D.

As shown in FIG. 5D, it was revealed that there was no difference in amount of all PAI-1, α-SMA, and fibronectin in the case of the NQO1-siRNA- and HO-1-siRNA-treated groups, compared to the control-siRNA-treated group. From these results, it was confirmed that the decreased expression of the ECM components by DMF was not associated with reactive oxygen species (ROS) through antioxidant enzyme.

Figure 6:
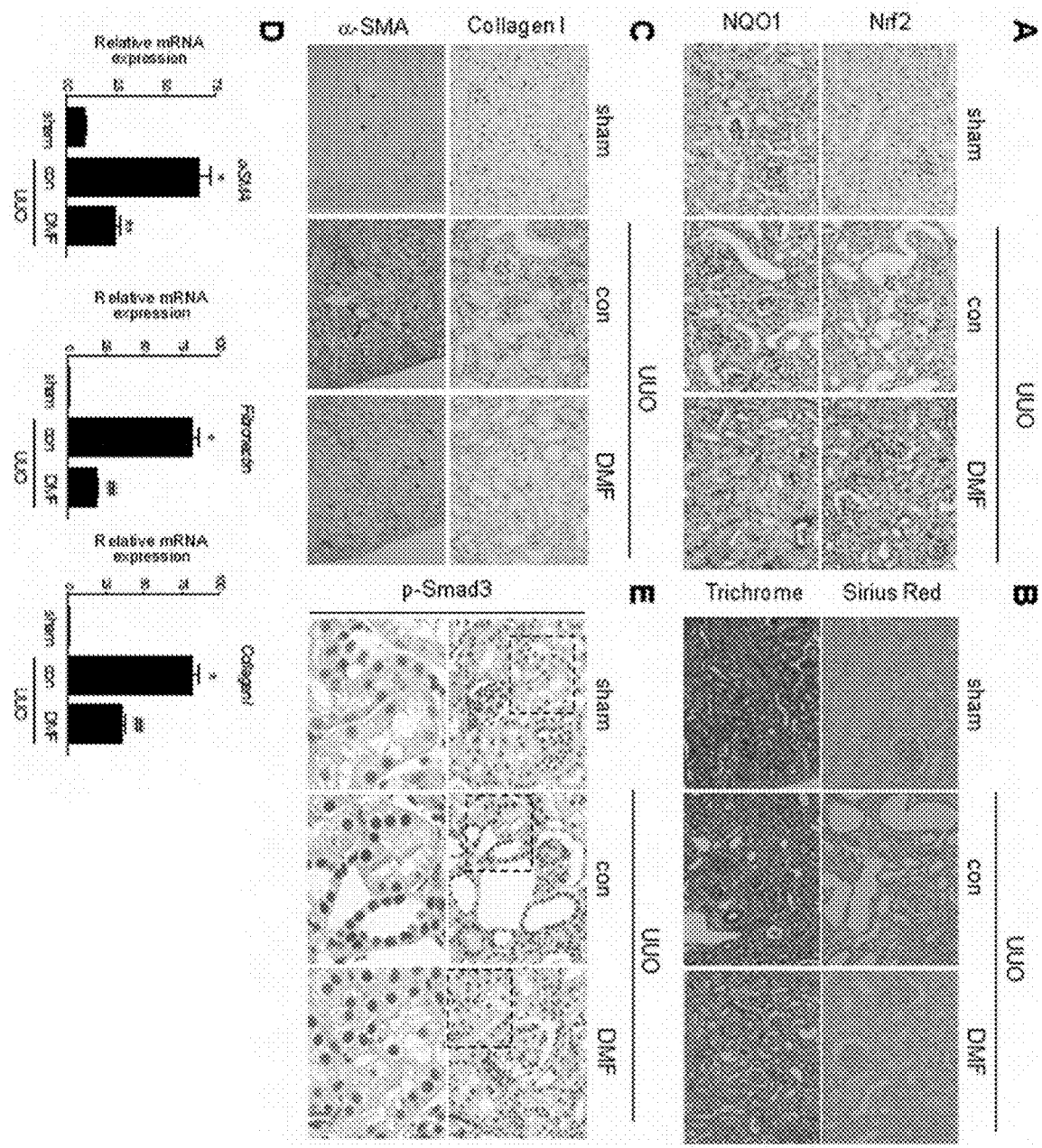
FIG. 6 is a diagram showing effects of DMF on renal fibrosis induced by unilateral ureteral obstruction (UUO) in an animal model.

Example 6: Determination of Effect of DMF on Renal Fibrosis Induced by Unilateral Ureteral Obstruction (UUO) Caused in Mice An effect of DMF on expression of the ECM components was determined through tissue staining in a mouse model. Specifically, expression levels of Nrf2 and NQO1 were determined through immunohistochemical staining, and an expression level of collagen type I was determined through Sirius-Red staining and trichrome staining. An animal test was performed using an UUO model, and mice were divided into a group in which the mice were fed with DMF by oral administration (gavage) (25 mg/kg), and a group in which the mice were not fed with DMF, and the mice were subjected to UUO surgery. After a week, the mice were anesthetized, and kidneys were extracted from the mice in each group. These experimental results are shown in FIG. 6.

As shown in FIG. 6A, it was revealed that the expression of Nrf2 and a target protein, NQO1, increased in the group in which the mice were fed with DMF.

As shown in FIG. 6B, it was revealed that the expression of collagen type I decreased in the group in which the mice were fed with DMF.

As shown in FIG. 6C, it was revealed that the expression of collagen type I and α-SMA decreased in the group in which the mice were fed with DMF.

As shown in FIG. 6D, the RNA expression of α-SMA, fibronectin, and collagen type I was determined through real-time PCR. As a result, it was revealed that the expression of the ECM components significantly decreased in the group in which the mice were fed with DMF.

As shown in FIG. 6E, it was revealed that the expression of phosphorylated Smad3 decreased in the group in which the mice were fed with DMF.

Hereinafter, Preparation Examples of the composition according to one exemplary embodiment of the present invention will be provided by way of example.

Preparation Example 1: Preparation of Pharmaceutical Formulations

1. Preparation of Powder

| DMF | 2 g |
|---|---|
| Lactose | 1 g |

The above-described components were mixed, and filled in an airtight pack to prepare a powder.

2. Preparation of Tablet

| DMF | 100 mg |
|---|---|
| Corn starch | 100 mg |
| Lactose | 100 mg |
| Magnesium stearate | 2 mg |

The above-described components were mixed together, and then tablet-pressed to prepare a tablet according to a conventional method of preparing a tablet.

3. Preparation of Capsule

| DMF | 100 mg |
|---|---|
| Corn starch | 100 mg |
| Lactose | 100 mg |
| Magnesium stearate | 2 mg |

The above-described components were mixed together, and then filled in a gelatin capsule to prepare a capsule according to a conventional method of preparing a capsule.

Preparation Example 2: Preparation of Foods

Foods including the DMF according to one exemplary embodiment of the present invention were prepared, as follows.

1. Preparation of Cooking Seasoning 20 to 95% by weight of the DMF was added to prepare cooking seasoning for promotion of health.

2. Preparation of Tomato Ketchup and Sauce 0.2 to 1.0% by weight of the DMF was added to a tomato ketchup or sauce to prepare a tomato ketchup or sauce for promotion of health.

3. Preparation of Flour-Based Foods

Foods for promotion of health were prepared by adding 0.5 to 5.0% by weight of the DMF to flour, and preparing bread, cakes, cookies, cracker, and noodles using the resulting mixture.

4. Preparation of Soups and Gravies 0.1 to 5.0% by weight of the DMF was added to soups and gravies to prepare livestock-processed products, and soups and gravies for noodles for promotion of health.

5. Preparation of Ground Beef

10% by weight of the DMF was added to ground beef to prepare ground beef for promotion of health.

6. Preparation of Dairy Products 5 to 10% by weight of the DMF was added to milk, and various dairy products such as butters and ice creams were prepared using the milk.

Preparation Example 3: Preparation of Drinks

1. Preparation of Carbonated Drinks 5 to 10% of sugar, 0.05 to 0.3% of citric acid, 0.005 to 0.02% of caramel, 0.1 to 1% of vitamin C were mixed as additives, and 79 to 94% of purified water was mixed with resulting mixture to prepare syrup. The syrup was sterilized at 85 to 98° C. for 20 to 180 seconds, and mixed with cooling water at a ratio of 1:4. Thereafter, 0.5 to 0.82% of carbonic acid gas was injected into the syrup to prepare a carbonated drink including the DMF according to one exemplary embodiment of the present invention.

2. Preparation of Health Drinks

Minor materials such as liquid fructose (0.5%), an oligosaccharide (2%), sugar (2%), a tablet salt (0.5%), and water (75%) were homogeneously blended with the DMF. The resulting mixture was sterilized instantly, and then packaged in small-sized packing containers such as vials, PET bottles, and the like to prepare health drinks.

3. Preparation of Vegetable Juices 5 g of the DMF was added to 1,000 ml of tomato or carrot juice to prepare vegetable juices for promotion of health.

4. Preparation of Fruit Juices 1 g of the DMF was added to 1,000 ml of apple or grape juice to prepare fruit juices for promotion of health.

While the present invention has been described with respect to the specific embodiments, it will be apparent to those skilled in the art that various changes and modifications may be made without departing from the spirit and scope of the invention as defined in the following claims.

The invention claimed is:

1. A method of treating renal fibrosis, comprising administering to a patient in need thereof a composition comprising dimethylfumarate (DMF) as an active ingredient.

2. A method of improving renal fibrosis, comprising administering to a patient in need thereof a food composition comprising DMF as an active ingredient.

* * * * *